(12) United States Patent
Engel

(10) Patent No.: US 9,772,295 B2
(45) Date of Patent: Sep. 26, 2017

(54) LAYING HEAD, FIBRE PLACEMENT DEVICE AND METHOD

(71) Applicant: AIRBUS DEFENCE AND SPACE GMBH, Ottobrunn (DE)

(72) Inventor: Franz Engel, Munich (DE)

(73) Assignee: Airbus Defence and Space GmbH, Taufkirchen (DE)

(*) Notice: Subject to any disclaimer, the term of this patent is extended or adjusted under 35 U.S.C. 154(b) by 129 days.

(21) Appl. No.: 14/924,947

(22) Filed: Oct. 28, 2015

(65) Prior Publication Data

US 2016/0114536 A1 Apr. 28, 2016

(30) Foreign Application Priority Data

Oct. 28, 2014 (DE) .................. 10 2014 015 831

(51) Int. Cl.
| | |
|---|---|
| *B32B 41/00* | (2006.01) |
| *G01N 21/88* | (2006.01) |
| *B29C 70/38* | (2006.01) |
| *G01N 21/84* | (2006.01) |

(52) U.S. Cl.
CPC ....... *G01N 21/8806* (2013.01); *B29C 70/388* (2013.01); *G01N 21/88* (2013.01); *G01N 2021/8472* (2013.01)

(58) Field of Classification Search
CPC .............. G01N 21/8806; G01N 21/88; G01N 2021/8472; B29C 70/388
USPC ...... 156/378, 379, 574, 64, 272.8, 351, 353, 156/358, 359, 379.8, 380.9, 433, 510, 156/511, 522, 523, 538, 577
See application file for complete search history.

(56) References Cited

U.S. PATENT DOCUMENTS

| | | | |
|---|---|---|---|
| 5,562,788 A | 10/1996 | Kitson | |
| 7,889,907 B2 | 2/2011 | Engelbart et al. | |
| 2005/0203657 A1* | 9/2005 | Engelbart | B29C 70/386 700/110 |
| 2006/0152712 A1 | 7/2006 | Engelbart et al. | |
| 2013/0228285 A1 | 9/2013 | Pause et al. | |
| 2014/0028831 A1 | 1/2014 | Cayment et al. | |

FOREIGN PATENT DOCUMENTS

| | | |
|---|---|---|
| DE | 10 2010 044 175 A1 | 5/2012 |
| DE | 10 2012 102 204 A1 | 9/2013 |

OTHER PUBLICATIONS

Official Action Report from corresponding German Priority Application No. 10 2014 015 831.4 dated Jun. 19, 2015.

* cited by examiner

*Primary Examiner* — Michael N Orlando
*Assistant Examiner* — Joshel Rivera
(74) *Attorney, Agent, or Firm* — Jenkins, Wilson, Taylor & Hunt, P.A.

(57) ABSTRACT

A laying head for a fibre placement device, in particular for fibre placement according to the AFP method, includes a placing roller which is permeable to laser light, at least in part, a laser light feed unit which is arranged in an inner space of the placing roller and a sensor which is designed and arranged to receive laser light reflected from a component on which the placing roller places a fibre band.

17 Claims, 1 Drawing Sheet

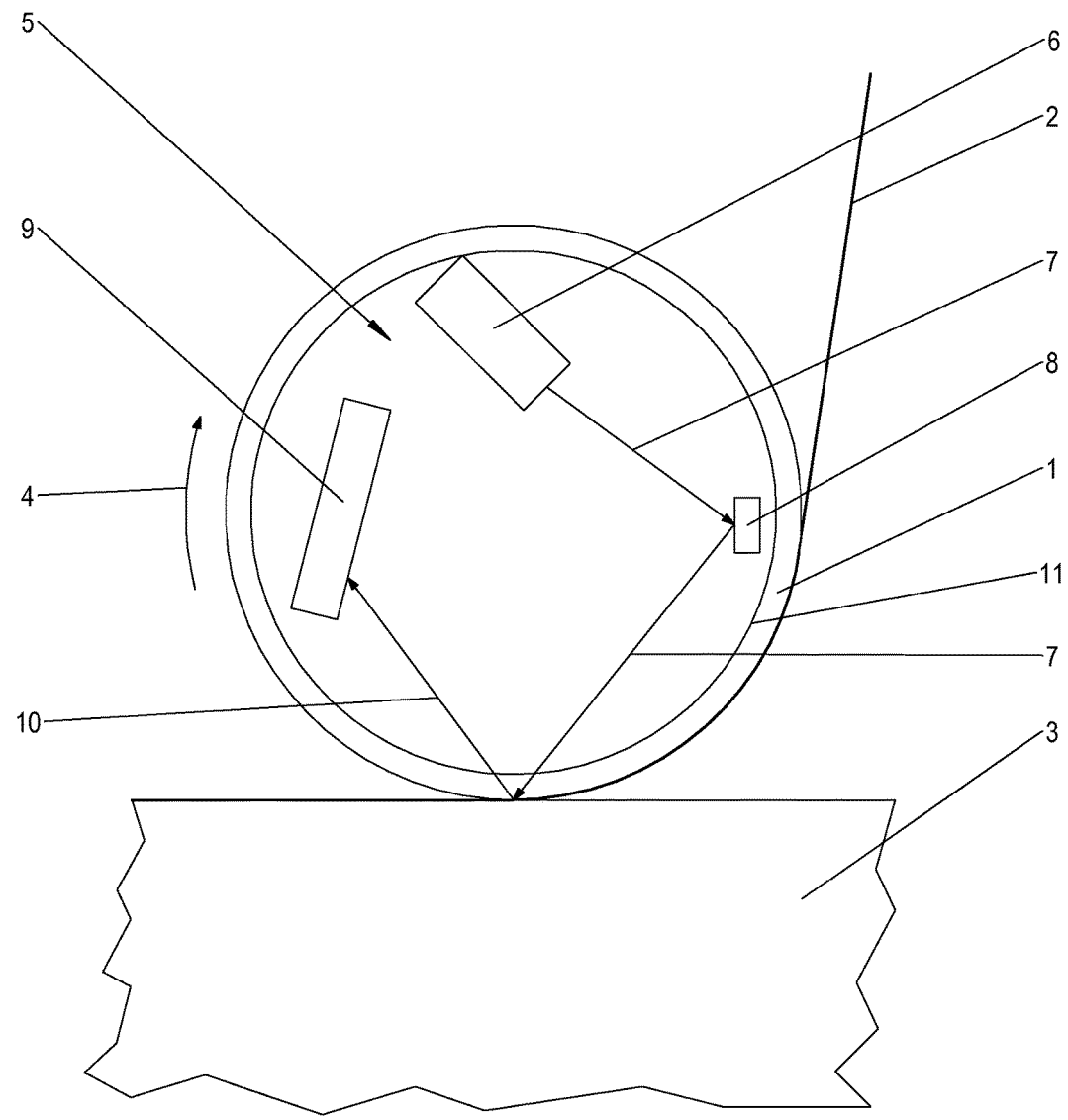

LAYING HEAD, FIBRE PLACEMENT DEVICE AND METHOD

FIELD OF THE INVENTION

The invention relates to a laying head for a fibre placement device, to a fibre placement device and to a method for examining a component which is manufactured using a fibre placement device.

BACKGROUND OF THE INVENTION

Fibre composite material, in particular in the aircraft industry, such as outer skin elements for aircraft, is often produced using automated fibre placement devices, which are referred to as AFP machines. In this case, relatively narrow strips of fibres, in particular carbon fibres which are embedded in a polymer matrix, are applied to a component to be manufactured or a corresponding tool. These fibre bands are placed along a predefined path on the three-dimensionally formed tool surface.

In order to manufacture a component, a plurality of individual placing steps is necessary. During these steps, a series of placing effects can occur, such as undesired overlapping of the individual fibre bands, gaps between said fibre bands or undulations, for example. These placing effects can optionally influence the mechanical properties of the manufactured component and should therefore be identified prior to using the component.

Conventionally, AFP-manufactured components are therefore examined by personnel during production. In this case, after each fibre layer has been applied, the quality of the fibre layer made from the individual fibre bands or from the layer is visually monitored with respect to the others. This is time-consuming and labour-intensive and is not always possible with a high level of certainty, in particular in the case of carbon fibres, because of the low contrast. Therefore, gaps between bands are difficult to detect since the black carbon fibres already lie on a plurality of layers of other carbon fibres, and therefore the gaps are not apparent as far as colour is concerned.

Sensors have therefore been proposed which sense the freshly placed fibre bands at a certain lateral distance from the laying head. This is disadvantageous in that errors are not detected when curves are placed in the component surface plane in particular, since a sensor following the laying head can lie outside the region to be examined in this case. Furthermore, examination results again have to be viewed and evaluated in a complex and labour-intensive manner. The space required for sensors on the laying head is also not negligible, as a result of which the installation space of the laying head and its freedom of movement are restricted.

SUMMARY OF THE INVENTION

One idea of the present invention is to propose a method for examining an AFP-manufactured component, which method eliminates the above-mentioned disadvantages, and a fibre placement device, by means of which this method can be carried out.

The laying head according to the invention for a fibre placement device is suitable in particular for fibre placement according to the AFP method. According to the invention, the laying head comprises a placing roller which is permeable to laser light, at least in part. This enables a component which is manufactured using the laying head to be examined for defects from an inner space of the placing roller in situ, i.e. during manufacture. A laser light feed unit and a sensor are arranged in the inner space of the placing roller. The sensor is designed and arranged to receive laser light reflected from the component on which the placing roller places a fibre band.

According to the invention, the laying head eliminates the disadvantage that a sensor cannot, for geometric reasons, examine every point of a fibre composite structure. The placing roller (also simply referred to as a "transparent placing roller" below), which is permeable to laser light, at least in part, makes it possible to examine a fibre band directly after being placed or even during placement. In contrast with the prior art, in which a sensor follows the laying head, the region to be examined on the component surface is therefore also, in the case of curves in the component surface plane, always in the field of view of the sensor. The laying head enables the component or the fibre band to be examined without costly use of personnel, since it can be automated. By integrating a sensor into the inner space of the placing roller, the laying head is not restricted in terms of installation space and freedom of movement.

In one embodiment, a mirror is arranged in the inner space of the placing roller in order to deflect the laser light from the laser light feed unit to the component at a predetermined angle. It can therefore be advantageously achieved that an angle between the laser light which radiates onto the component and the laser light which is reflected from the component is greater than it would be without a mirror. This can be advantageous when the sensor detects a height profile of the component using the reflected laser light.

The sensor advantageously has a CCD sensor. CCD sensors (charge-coupled device), which are commonly used in cameras, are also referred to simply as "camera chips". These are available in small sizes and therefore the limited inner space of the placing roller is sufficient for this.

The sensor can be dimensioned in such a way that, for example, taking into account a reflection angle at which reflected laser light from the component falls on the sensor, light reflected from the component is substantially picked up by the sensor. "Substantially", within the context of the invention, means that light reflected from the component is sufficiently picked up by the sensor in order to obtain information from the surface irradiated by the laser light. This information can contain, for example, the height profile of the irradiated surface.

In particular in an arrangement in which the reflected light falls on the sensor at a particularly flat angle, it can be advantageous for the sensor to be composed of a plurality of sensors arranged next to one another or to have a correspondingly large ratio of length to width.

According to one aspect of the invention, a laser is arranged in the inner space of the placing roller as a laser light feed apparatus. A simple construction is achieved thereby.

According to another aspect, a laser can be arranged outside the placing roller. In this case, laser light emitted by the laser can be deflected onto an inner side of the placing roller by means of the laser light feed unit. Correspondingly, the laser light can be deflected onto the component to be examined. For example, in this case the laser light feed unit can have a mirror or glass fibres.

According to one variant of the laying head, optics are arranged in the inner space of the placing roller, which optics are suitable for deflecting laser light reflected from the component onto the sensor. Therefore, a mirror for example can deflect the laser light as desired and/or as required in order to optimally make use of the space in the inner space or in order to achieve an advantageous angle of incidence of the light into the sensor. Otherwise, beam expansion or beam focusing can be desired. It is also conceivable for the optics to be designed and arranged in such a way that the sensor can be positioned outside the inner space.

The term "fibre band" corresponds to the geometries typically used in the AFP method. However, this is not to be considered as restrictive in the context of the invention. Therefore, all geometries of fibres which are embedded in a polymer matrix can be understood thereby. Such two-dimensional polymer-fibre structures include rovings, yarns, unidirectional composites, prepregs or similar semi-finished products common in fibre composite technology.

The laser light feed apparatus, the sensor and optionally the minor and/or the optics are in particular arranged in such a way that they are placed independently of the rotation of the placing roller. This is preferably achieved in that the parts mentioned are connected to the laying head in a stationary manner.

The placing roller preferably contains a flexible material or is manufactured from this material. This can be advantageous for placing or pressing the fibre band onto the component.

An angle sensor and/or a position sensor can moreover be arranged on the placing roller, in particular in the inner space of the placing roller, which sensor is suitable for detecting an angle and/or a position of the fibre band (2). A signal of the angle sensor and/or position sensor can be used to trigger the sensor or the laser respectively.

A fibre placement device according to the invention comprises a laying head according to the invention. The fibre placement device can be a device for automated fibre placement according to the AFP method. A fibre placement device according to the invention does not only have the known advantages for producing a fibre-reinforced fibre composite part, but is also able to examine the fibre-reinforced fibre composite part for possible defects in situ, i.e. directly during manufacture thereof. These defects can be gaps, overlaps, corrugations or other common defects.

In a method according to the invention for examining a component which is manufactured using a fibre placement device, laser light is radiated from an inner space of a placing roller, which is permeable to this laser light, at least in part, to a fibre band which is placed onto a component or tool by a placing roller, and reflected light is picked up using a sensor. The component is preferably produced using a fibre placement device which operates according to the AFP method, in particular using a fibre placement device which contains a laying head according to the invention. All the features which have been explained with regard to the function of the laying head according to the invention or the fibre placement device according to the invention should also apply to the method according to the invention as disclosed.

The reflected light may be evaluated with regard to a height profile of the component. This enables particularly good detection of possible defects in the placed fibre band, between two or more placed fibre bands or any other way in the component.

According to an advantageous variant, the laser light is radiated onto the placed fibre band in such a way that regions which are adjacent to the placed fibre band are also irradiated. Therefore, defects which not only relate to the currently placed fibre band but also those between two or more placed fibre bands or any other way in the component can be identified easily.

Furthermore, radiating and/or picking up the laser light by means of the laser or the sensor respectively can be triggered by the position sensor and/or the angle sensor.

Other advantageous embodiments of the present invention are the subject matter of other dependent claims.

BRIEF DESCRIPTION OF THE DRAWING

Other embodiments and advantages of the invention will be explained in more detail hereinafter on the basis of a preferred embodiment and with reference to a schematic drawing.

FIG. 1—The single FIGURE schematically shows a cross section through a placing roller of the laying head according to the invention, which roller places just one fibre band.

DETAILED DESCRIPTION OF EMBODIMENTS OF THE INVENTION

The FIGURE shows those parts of a laying head according to the invention which are relevant to the invention. A transparent placing roller 1 places a fibre band 2 made of carbon fibres onto a component 3. In this case, the placing roller 1 rotates in the direction of the arrow 4 and presses the fibre band 2 onto the component 3 at a certain pressure during the placing operation. Depending on which material is used for the polymer matrix in which the fibres are located, i.e. for example a thermoplastic or a thermosetting plastics material, correspondingly adjusted heating units (not shown) can bring about curing or consolidation of the matrix material after the placing operation.

A laser 6 is arranged in an inner space 5 of the placing roller 1 and emits laser light 7 to a minor 8, which light is reflected by said mirror and impinges on an inner side 11 of the placing roller and then on the component 3. The laser light 7 impinges on the component 3 in a region in which the fibre band 2 contacted the component 3 immediately before and to which region said fibre band remains adhered due to the adhesiveness of the fibre band 2 and the contact pressure of the placing roller 1.

In this embodiment, the region in which the fibre band has been placed is directly adjacent to another fibre band which has been placed parallel to the current fibre band 2. The intended geometry of the fibre placement is such that the two fibre bands can come to lie next to one another without an intermediate space. The fibre band placed first cannot be seen in the side view in the FIGURE.

The laser light 7 is reflected from the region of the component 3 on which it impinges, at a corresponding angle according to optical laws and impinges on a sensor 9. In this embodiment, the sensor 9 is a CCD sensor, which is common in cameras. Said sensor can receive the reflected light 10 in a spatially resolved manner and with regard to a height profile and pass it to a suitable evaluation unit (not shown) for an evaluation.

In this example, there is a gap between the currently placed fibre band 2 and the previously placed fibre band, which gap is greater than a predetermined threshold value. This is detected by the evaluation unit in accordance with the spatially resolved height profile. This detected defect can now be correspondingly acted on.

The laser 6, the minor 8 and the sensor 10 are arranged in the inner space 5 of the placing roller 1 in such a way that they are placed independently of the rotation of the placing roller 1. This is achieved in that the parts mentioned are connected to the laying head in a stationary manner. The visual monitoring of possible defects on the component 3 is thereby always directed to that region in which a fibre band 2 has most recently been placed. The same applies correspondingly to those parts which are optionally additionally or alternatively arranged in the inner space 5 of the placing roller 1 instead of the laser 6, the mirror 8 and the sensor 10.

Such additional or alternative parts are, according to variants of the embodiment, on the one hand, glass fibres, by means of which the laser light is guided into the inner space 5 of the placing roller 1. In this variant, the laser is arranged at any point on the laying head. On the other hand, optics can be used which manipulate the laser light 7, 8 at different points. Such manipulations can be expansions or focusing of the laser beam, and deflections and redirections. This can occur as desired and as required in order to optimally use the space in the inner space 5 of the placing roller 1, and in order to optimise the resolution, depth of focus or accuracy of the visual monitoring. Such optics are known and are not explained in more detail here.

The material of the placing roller 1 is permeable, at least in part, to wavelengths of the laser light 7 which is emitted by the laser 6. Further properties of the material can be a certain elasticity and temperature resistance. Depending on the temperature generated by the optionally present heating units, the material should keep its mechanical and visual properties during heating as far as possible. Suitable materials can be plastics, such as polyol, polyethylene, polycarbonate, polymethyl methacrylate or glasses or crystals, e.g. silicon dioxide.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding German Application No. 102014015831.4, filed Oct. 28, 2014 are incorporated by reference herein.

What is claimed is:

1. A laying head for a fibre placement device, comprising:
    a placing roller which is permeable to laser light, at least in part;
    a laser light feed unit which is arranged in an inner space of the placing roller; and
    a sensor which is designed and arranged to receive laser light reflected from a component on which the placing roller places a fibre band.

2. The laying head according to claim 1, wherein a mirror is arranged in the inner space of the placing roller in order to deflect the laser light from the laser light feed unit to the component at a predetermined angle.

3. The laying head according to claim 1, wherein the sensor comprises a CCD sensor.

4. The laying head according to claim 3, wherein the sensor is dimensioned in such a way that light reflected from the component is substantially picked up by the sensor.

5. The laying head according to claim 1, wherein a laser is arranged in the inner space of the placing roller as a laser light feed apparatus.

6. The laying head according to claim 1, wherein a laser is arranged outside the placing roller and in that laser light emitted by the laser can be deflected onto an inner side of the placing roller by means of the laser light feed unit.

7. The laying head according to claim 6, wherein the laser light feed unit comprises a minor or glass fibres.

8. The laying head according to claim 1, wherein optics are arranged in the inner space of the placing roller, which optics are suitable for deflecting laser light reflected from the component onto the sensor.

9. The laying head according to claim 1, wherein the placing roller contains a flexible material.

10. The laying head according to claim 1, wherein an angle sensor and/or a position sensor is arranged on the placing roller, which sensor is suitable for detecting an angle and/or a position of the fibre band.

11. A fibre placement device for automated fibre placement according to the AFP method, comprising a laying head, the laying head comprising:
    a placing roller which is permeable to laser light, at least in part;
    a laser light feed unit which is arranged in an inner space of the placing roller; and
    a sensor which is designed and arranged to receive laser light reflected from a component on which the placing roller places a fibre band.

12. A method for examining a component which is manufactured using a fibre placement device for automated fibre placement according to the AFP method, comprising a laying head, the laying head comprising:
    a placing roller which is permeable to laser light, at least in part;
    a laser light feed unit which is arranged in an inner space of the placing roller; and
    a sensor which is designed and arranged to receive laser light reflected from a component on which the placing roller places a fibre band, the method comprising:
    radiating laser light from the inner space of the placing roller, which is permeable to the laser light, at least in part, to the fibre band which is placed onto a component or tool by the placing roller; and
    picking up reflected light by a sensor.

13. The method according to claim 12, wherein the reflected light is evaluated with regard to a height profile of the component.

14. The method according to claim 12, wherein the laser light is radiated onto the placed fibre band in such a way that regions which are adjacent to the placed fibre band are also irradiated.

15. The method according to claim 12, wherein radiating and/or picking up the laser light is triggered by a position sensor and/or an angle sensor, which can detect a position and/or an angle of the placed fibre band.

16. The laying head according to claim 1, wherein the laying head is used for fibre placement according to the AFP method.

17. The laying head according to claim 9, wherein the placing roller is manufactured from the flexible material.

* * * * *

UNITED STATES PATENT AND TRADEMARK OFFICE
CERTIFICATE OF CORRECTION

PATENT NO. : 9,772,295 B2  
APPLICATION NO. : 14/924947  
DATED : September 26, 2017  
INVENTOR(S) : Franz Engel It is certified that error appears in the above-identified patent and that said Letters Patent is hereby corrected as shown below:

In the Claims

In Column 6, Line 9 (within Claim 7):  
Replace "minor"  
With --mirror--.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*